United States Patent [19]

Ward

[11] Patent Number: 4,961,920

[45] Date of Patent: Oct. 9, 1990

[54] PHOTOTHERAPEUTIC MONOVINYL AND DIVINYL ETHER-LINKED DIMERS

[75] Inventor: A. David Ward, Burnside, Australia

[73] Assignee: Luminis Pty, Ltd., Adelaide, Australia

[21] Appl. No.: 352,793

[22] Filed: May 16, 1989

[30] Foreign Application Priority Data

Dec. 8, 1988 [AU] Australia .................................. PJ1860

[51] Int. Cl.$^5$ ..................... A61K 49/00; A61K 31/40; A61K 37/04; C07D 259/00
[52] U.S. Cl. ........................................ 424/9; 514/12; 514/410; 530/387; 530/388; 530/389; 530/391; 540/145
[58] Field of Search .................. 540/145; 514/12, 183; 530/387, 388, 389, 391; 424/9

[56] References Cited

U.S. PATENT DOCUMENTS

| | | | |
|---|---|---|---|
| 4,500,507 | 2/1985 | Wong | 540/145 |
| 4,512,762 | 4/1985 | Spears . | |
| 4,634,557 | 1/1987 | Sato et al. | 540/145 |
| 4,649,151 | 3/1987 | Dougherty et al. | 540/145 |
| 4,727,027 | 2/1988 | Wiesehahn et al. | 514/6 |
| 4,748,120 | 5/1988 | Wiesehahn | 514/6 |
| 4,753,958 | 6/1988 | Weinstein | 514/6 |

OTHER PUBLICATIONS

Diamond et al., *Lancet* (1972) 2:1175–1177.
Dougherty et al., *Cancer Res.* (1978) 38:2628–2635.
Dougherty et al., "Porphyrin Localization and Treatment of Tumors" (1984), Alan R. Liss, Inc., pp. 301–314.
Dougherty et al., *CRC Critical Rev. in Oncology/Hematology* (1984) 2:83–116.
Gregorie et al., *Ann. Surg.* (1968) 167:820–828.
Mew et al., *J. Immunol.* (1983) 130:1473–1477.
Mew et al., *Cancer Res.* (1985) 45:4380–4386.
Weishaupt et al., *Cancer Res.* (1976) 36:2326–2329.
Morgan et al., *Chem. Abstracts* (1985) 102:61981s.
Richter et al., *JNIC* (1987) 79(6):1327–1331.
Pangka et al., *Chem. Abstracts* (1986) 104:207015v.
Dougherty et al., *Adv. Exp. Med. Biol.* (1983) 160:3–13.
Kessell et al., *Photochem. Photobiol.* (1987) 46(5):563–568.
Scourides et al., *Cancer Res.* (1987) 47:3439–3445.
Pandey et al., *Cancer Res.*
Morris et al., *Tetrahedron Letters* (1988) 29:2501–2504.
Lipson et al., *J. Natl. Cancer Inst.* (1961) 26:1–8.

Primary Examiner—Mukund J. Shah
Assistant Examiner—E. C. Ward
Attorney, Agent, or Firm—Irell & Manella

[57] ABSTRACT

Pure dimer compounds prepared and shown to be effective photosensitizing agents are of the formula

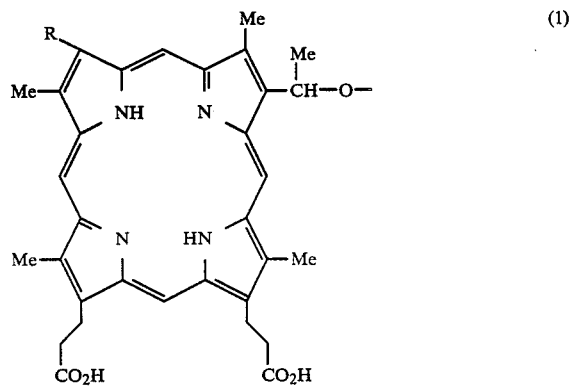

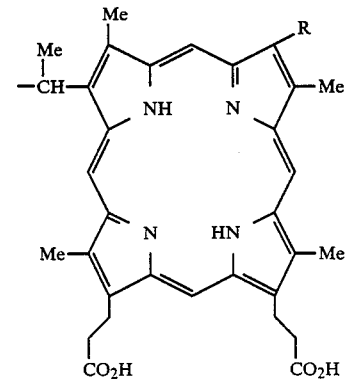

wherein one R is vinyl and the other R is hydroxyethyl or vinyl and the pharmaceutically acceptable esters and salts thereof in isolated form.

9 Claims, No Drawings

PHOTOTHERAPEUTIC MONOVINYL AND DIVINYL ETHER-LINKED DIMERS

TECHNICAL FIELD

The invention relates to the treatment and diagnosis of tumors and to other in vivo and in vitro photosensitization methods associated with the irradiation of porphyrins. In particular, it concerns compounds useful in these procedures which are the monovinyl and divinyl ether-linked dimers of porphyrin ring systems.

BACKGROUND ART

The use of porphyrin compounds in photodynamic therapy and related uses is well known, and numerous publications concerning various compositions useful in these applications have appeared. The development of the technology stems from the use of "hematoporphyrin derivative" (HPD) which is a complex mixture formed when hematoporphyrin dichloride is treated with a mixture of sulfuric and acetic acid according to the procedure of Lipson, R. L. et al., *J Nat Cancer Inst* (1961) 26:1–8. A substantial improvement in the efficacy of this type of drug was effected by Dougherty et al., U.S. Pat. No. 4,649,151, who showed that a fraction of HPD consisting of aggregates of 10 kd or greater was considerably more effective than HPD itself. This fraction, still a complex mixture, is commercially available under the trademark Photophrin ® purified hematoporphyrin derivative.

The above-referenced U.S. Pat. No. 4,649,151 further describes in detail the method of phototherapeutic treatment using the fraction prepared. While treatment of tumors is exemplified, and it is known that the active compounds home to tumor tissue, it is clear that other therapeutic, diagnostic, and industrial applications of the photosensitizing ability of these materials are not excluded. More recent publications have specified particular alternative indications. For example, photosensitizing porphyrins are useful in the detection and treatment of atherosclerotic plaques, as described in U.S. Pat. Nos. 4,512,762 and 4,574,682. U.S. Pat. Nos. 4,500,507 and 4,485,806 describe the use of radiolabeled porphyrin compounds, including HPD, for tumor imaging. U.S. Pat. No. 4,753,958 to the University of California describes the use of topical application of porphyrin sensitizers for diagnosis and treatment of skin diseases. U.S. Pat. No. 4,748,120 describes the use of photosensitizers in the treatment of whole blood or blood components. Photochemical decontamination treatment of blood and components is also described in U.S. Pat. No. 4,727,027 where the photosensitizer is furocumarin and its derivatives. In addition, virus are inactivated in therapeutic protein compositions in vitro as disclosed in U.S. Pat. No. 4,268,947.

It is understood that the purified composition marketed as Photophrin ® II purified hematoporphyrin derivative is a complex mixture. It is known that the mixture contains porphyrins joined by ether linkages (Dougherty, T. J. et al, *Adv Exp Med Biol* (1983) 160:3–13) and Kessel, D. et al., *Photochem Photobiol* (1987) 36:463–568 has shown that ester-linked porphyrins are contained in this mixture. Scourides, P. A. et al., *Cancer Res* (1987) 47:3439–3445 synthesized a mixture of oligomers of ether-linked porphyrins starting from hematoporphyrin dimethyl esters, which was active in assays for photodynamic treatment of tumors, but was as complex a mixture as the Photophrin ® II preparation. Dimers of hematoporphyrin joined by ester linkages have also been prepared by Pandey, R. K. et al., *Cancer Res* (in press) and these dimers were shown to be absent from the mixture in the Photophrin ® II composition, as well as active in an in vitro assay.

Thus, while it is known that complex mixtures of porphyrin derivatives obtained in a prescribed manner are useful and effective in various applications where photosensitizing activity is desirable, individual purified components which are responsible for the activity of the complex mixture have not been prepared and identified. It has now been found that the ether-linked monovinyl and divinyl dimers of porphyrin nuclei are active and effective in these applications. A summary of this discovery was published by the inventors herein in *Tetrahedron Letters* (1988) 29:2501–2504, which was mailed to subscribers on May 17, 1988. The disclosure of this paper is incorporated herein by reference.

DISCLOSURE OF THE INVENTION

The invention provides purified, isolated materials which can be definitively characterized by structural formula and which are useful in the photosensitizing applications known for hematoporphyrin derivative and the more effective Photophrin ® purified hematoporphyrin derivative. These compounds are ether-linked dimers containing at least one vinyl substituent. The preparation of these purified compounds has not heretofore, to the best of our knowledge, been disclosed.

Thus, in one aspect, the invention is directed to a compound of the formula:

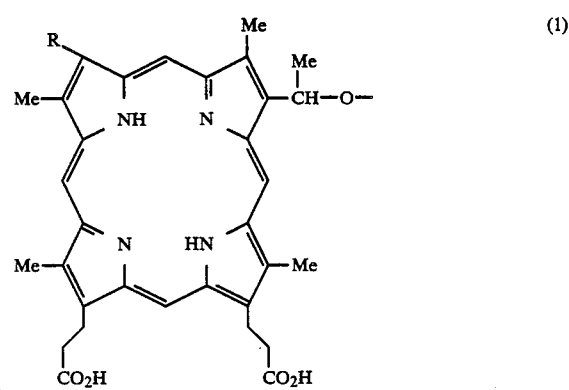

(1)

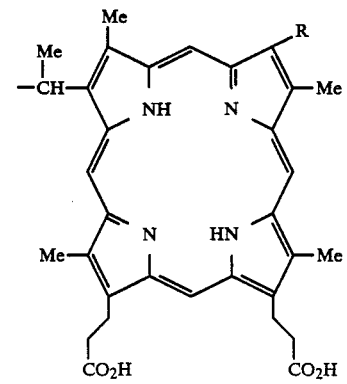

wherein one R is vinyl and the other R is hydroxyethyl or vinyl, and the pharmaceutically acceptable esters and salts thereof.

In other aspects, the invention is directed to pharmaceutical compositions containing effective amounts of the compounds of formula (1), and to methods of photosensitizing and detecting target materials using these compounds or compositions.

MODES OF CARRYING OUT THE INVENTION

The invention is directed to isolated forms of the compounds represented by formula (1). These compounds are ether-linked dimers containing at least one vinyl substituent in the A or B ring of one member of the pair. It is understood that formula (1) in fact represents several isomeric compounds as well as a purified mixture of specified isomers depending on the position of the ether linkage relative to the remaining R substituents. The mixture of isomers of the invention is most conveniently prepared starting with 2(4)-monohydroxyethyl4(2)-monovinyl deuteroporphyrin—i.e., a mixture of deuteroporphyrins wherein the monohydroxyethyl substituent is substituted on the A ring in one isomer and on the B ring in the other, and the vinyl substituent vice versa. Thus, the products will be a mixture of isomers wherein the ether linkage is formed between the A rings of the members of the dimer, between the two B rings of the members of the dimer, and with an A-B linkage. The A-B linkage is a single structural isomer in the case of the divinyl form, but a mixture of structural isomers in the case of the monohydroxyethyl/monovinyl form. The compounds of formula (1) are intended to include these specified structural isomers. A particular structural isomer as shown in FIG. 1 is used for convenience.

The compounds of the invention may be used as the free acids as shown, or one or more of the carboxyethyl substituents of the C and D rings can be converted to the pharmaceutically acceptable salts or esters. Preferred as pharmaceutically acceptable esters are esters formed from the hydrocarbyl alcohols of 1-6carbons, such as methyl, ethyl, propyl, isopropyl, butyl, 2-butyl, 2-pentyl, isopentyl, or 2-hexyl and the like. Especially preferred are ethyl and methyl esters. Methods to convert acids to esters and to deesterify carboxylic groups are well known in the art.

The compounds of the invention can also be administered as the pharmaceutically acceptable salts. Salts may be formed from inorganic bases such as sodium, potassium, or calcium hydroxide and from organic bases such as various amines, for example choline or piperidine. It is understood that the free acid forms of the compounds as shown will effectively exist in "salt" form at physiological pH.

It is also understood that the components of the structural isomeric mixtures described above and represented in composite by formula (1) can be separated into individual components using standard chromatographic or other separation techniques and the individual structural isomers used in the methods of the invention.

In addition, the compounds of formula (1) contain at least two chiral centers, and can be used in the methods of the invention either as mixtures of stereoisomers, racemic mixtures, or as isolated compounds of a single stereoisomer.

MODIFIED FORMS OF THE INVENTION COMPOUNDS

The possibility of using compositions which consist essentially of the above-defined compounds as active ingredient make possible the derivatization of the dimer contained in order to provide a specific targeting mechanism. Commonly used target-specific components include monoclonal antibodies and ligands which bind to a cellular receptor. The compositions can also be conveniently labeled.

The target-specific component can then be, for example, an immunoglobulin or portion thereof or a ligand specific for a particular receptor. The immunoglobulin component can be any of a variety of materials. It may be derived from polyclonal or monoclonal antibody preparations and may contain whole antibodies or immunologically reactive fragments of these antibodies such as F(ab')$_2$, Fab, or Fab' fragments. Use of such immunologically reactive fragments as substitutes for whole antibodies is well known in the art. See, for example, Spiegelberg, H. L., in "Immunoassays in the Clinical Laboratory" (1978) 3:1-23.

Polyclonal anti-sera are prepared in conventional ways by injecting a suitable mammal with antigen to which antibody is desired, assaying the antibody level in serum against the antigen, and preparing anti-sera when the titers are high. Monoclonal antibody preparations may also be prepared conventionally such as by the method of Koehler and Milstein using peripheral blood lymphocytes or spleen cells from immunized animals and immortalizing these cells either by viral infection, by fusion with myelomas, or by other conventional procedures, and screening for production of the desired antibodies by isolated colonies. Formation of the fragments from either monoclonal or polyclonal preparations is effected by conventional means as described by Spiegelberg, H. L., supra.

Particularly useful antibodies include the monoclonal antibody preparation CAMAL1 which can be prepared as described by Malcolm, A., et al., *Ex Hematol* (1984) 12:539-547; polyclonal or monoclonal preparations of anti-M1 antibody as described by Mew, D., et al., *J Immunol* (1983) 130:1473-1477 (supra) and B16G antibody which is prepared as described by Maier, T., et al., *J Immunol* (1983) 131:1843; Steele, J. K., et al., *Cell Immunol* (1984) 90:303.

The foregoing list is exemplary and certainly not limiting; once the target tissue is known, antibody specific for this tissue may be prepared by conventional means. Therefore the invention is applicable to effecting toxicity against any desired target.

The ligand specific for receptor, refers to a moiety which binds a receptor at cell surfaces, and thus contains contours and charge patterns which are complementary to those of the receptor. It is well understood that a wide variety of cell types have specific receptors designed to bind hormones, growth factors, or neurotransmitters. However, while these embodiments of ligands specific for receptor are known and understood, the phrase "ligand specific for receptor", as used herein, refers to any substance, natural or synthetic, which binds specifically to a receptor.

Examples of such ligands include the steroid hormones, such as progesterone, estrogens, androgens, and the adrenal cortical hormones; growth factors, such as epidermal growth factor, nerve growth factor, fibroblast growth factor, and so forth; other protein hormones, such as human growth hormone, parathyroid hormone, and so forth; and neurotransmitters, such as acetylcholine, serotonin, and dopamine. Any analog of these substances which succeeds in binding to the receptor is also included.

The conjugation of the target-cell-specific component to the dimers can be effected by any convenient means. For proteins, such as Ig and certain receptor ligands, a direct covalent bond between these moieties may be effected, for example, using a dehydrating agent such as a carbodiimide. A particularly preferred method of covalently binding the dimers to the immunoglobulin moiety is treatment with 1-ethyl-3-(3-dimethylamino propyl) carbodiimide (EDCI) in the presence of a reaction medium consisting essentially of dimethyl sulfoxide (DMSO).

Of course, other dehydrating agents such as dicyclohexylcarbodiimide or diethylcarbodiimide could also be used as well as conventional aqueous and partially aqueous media.

Nonprotein receptor ligands can be conjugated to the dimers according to their relevant functional groups by means known in the art.

The active moieties of the conjugate may also be conjugated through linker compounds which are bifunctional, and are capable of covalently binding each of the two active components. A large variety of these linkers is commercially available, and a typical list would include those found, for example, in the catalog of the Pierce Chemical Co. These linkers are either homo- or heterobifunctional moieties and include functionalities capable of forming disulfides, amides, hydrazones, and a wide variety of other linkages Other linkers include polymers such as polyamines, polyethers, polyamine alcohols, derivatized to the components by means of ketones, acids, aldehydes, isocyanates, or a variety of other groups.

The techniques employed in conjugating the active moieties of the conjugate to the target-specific component include any standard means and the method for conjugation does not form part of the invention. Therefore, any effective technique known in the art to produce such conjugates falls within the scope of the invention, and the linker moiety is accordingly broadly defined only as being either a covalent bond or any linker moiety available in the art or derivable therefrom using standard techniques.

The dimer compounds per se or the conjugates may be further derivatized to a compound or ion which labels the drug. A wide variety of labeling moieties can be used, including radioisotopes and fluorescent labels. Radioisotope labeling is preferred, as it can be readily detected in vivo.

The compounds of the invention which are used alone or as conjugates of dimer with a specific binding substance can be labeled with radioisotopes by coordination of a suitable radioactive cation in the porphyrin system. Useful cations include technetium and indium. In the conjugates, the specific binding moieties can also be linked to label through reactive substituents contained in them.

In general compounds of the invention can be administered or used in vitro methods as shown or when complexed to appropriate metal ions. As is generally understood in the art, the porphyrin nucleus can be treated with an appropriate ion such as magnesium ion, zinc ion, stannous ion, and the like to obtain the metal complex. As stated above, the metal ion may also be a radiolabel. The nature and desirability of the inclusion of a metal ion in the porphyrin nucleus depends on the specific application for which the compound is intended. When the inclusion of a metal ion is desired, the desired metal ion can be inserted using the appropriate metal salts under known conditions. For example, zinc ion can be introduced by treating the compound with zinc acetate in 1:1 methylene chloride:methanol.

ADMINISTRATION AND USE

The defined dimer compositions and their conjugates with target-specific substances of the invention are useful, in general, in the manner known in the art for hematoporphyrin derivative and for Photofrin ® II compositions. These compositions are useful in sensitizing neoplastic cells or other abnormal tissue to destruction by irradiation using visible light—upon photoactivation, the compositions have no direct effect, nor are they entered into any biological event; however the energy of photoactivation is believed to be transferred to endogenous oxygen to convert it to singlet oxygen. This singlet oxygen is thought to be responsible for the cytotoxic effect. In addition, the photoactivated forms of porphyrin fluorescence which fluoresce can aid in localizing the tumor. Thus, the dimer compounds of the invention are not consumed or altered in exerting their biological effects.

Typical indications, known in the art, include destruction of tumor tissue in solid tumors, dissolution of plaques in blood vessels (see, e.g., U.S. Pat. No. 4,512,762); treatment of topical conditions such as acne, athletes foot, warts, papilloma, and psoriasis and treatment of biological products (such as blood for transfusion) for infectious agents, since the presence of a membrane in such infectious agents promotes the accumulation of the dimer.

The conjugates of the invention, or the dimers when employed alone are formulated into pharmaceutical compositions for administration to the subject or applied to an in vitro target using techniques known in the art generally. A summary of such pharmaceutical compositions may be found, for example, in *Remington's Pharmaceutical Sciences,* Mack Publishing Co., Easton, Pennsylvania, latest edition.

The conjugates or compounds of the invention taken alone can be used in the systemic treatment of tumors and neoplastics made as bronchial, cervical, esophageal or colon cancer and for the diagnosis of same. The conjugates and dimers of the present invention, labeled or unlabeled, can be administered systemically, in particular by injection, or can be used topically. The dimers or their conjugates can be used singly or as components of mixtures.

Injection may be intravenous, subcutaneous, intramuscular, or, even intraperitoneal. Injectables can be prepared in conventional forms, either as liquid solutions or suspensions, solid form suitable for solution or suspension in liquid prior to injection, or as emulsions. Suitable excipients are, for example, water, saline, dextrose, glycerol and the like. Of course, these compositions may also contain minor amounts of nontoxic, auxiliary substances such as wetting or emulsifying agents, pH buffering agents and so forth.

Systemic administration can also be implemented through implantation of a slow release or sustained release system, by suppository, or, if properly formulated, orally. Formulations for these modes of administration are well known in the art, and a summary of such methods may be found, for example, in *Remington's Pharmaceutical Sciences* (supra).

For diagnosis, the compounds or their conjugates may be used along with, or may be labeled by, a radioisotope or other detecting means. Alternatively, the fluorescence induced in the dimer may be used for detection.

If treatment is to be localized, such as for the treatment of superficial tumors or skin disorders, the active conjugates or dimers may be topically administered using standard topical compositions involving lotions, suspensions, or pastes.

The quantity of conjugate or dimer to be administered depends on the choice of active ingredient, the condition to be treated, the mode of administration, the individual subject, and the judgment of the practitioner. Depending on the specificity of the preparation, small or larger doses may be needed. For compositions which are highly specific to target tissue, such as those which comprise conjugates of the dimer with a highly specific monoclonal immunoglobulin preparation or specific receptor ligand, dosages in the range of 0.05-1 mg/kg are suggested. For compositions which are less specific to the target tissue, larger doses, up to 1-10 mg/kg may be needed. The foregoing ranges are merely suggestive, as the number of variables in regard to an individual treatment regime is large and considerable excursions from these recommended values are expected.

In addition to in vivo use, the compounds of the invention can be used in the treatment of materials in vitro to destroy harmful viruses or infectious agents. For example, blood plasma or blood which is to be used for transfusion or banked for future transfusion can be treated with the compounds of the invention and irradiated to effect sterilization. In addition, biological products such as Factor VIII which are prepared from biological fluids can be irradiated in the presence of the compounds of the invention to destroy contaminants.

PREPARATION OF THE INVENTION COMPOUNDS

The above-referenced *Tetrahedron Letters* paper describes the preparation of the ether-linked dimer bearing a 1-hydroxyethyl substituent on each porphyrin, and discloses that the divinyl and monovinyl dehydration products can be detected as side products of the reactions. These materials are more conveniently prepared, however, by treatment of 2(4)-monohydroxyethyl-4(2)monovinyl deuteroporphyrin in a suitable solvent, preferably an aprotic relatively nonpolar solvent, with hydrogen bromide. Both the monovinyl and divinyl materials are formed under these conditions, and can be conveniently separated by thin layer chromatography or by other standard chromatographic methods. Alternative approaches to the synthesis of the dimeric compounds of the invention can also be employed; as shown below, the separated monovinyl and divinyl ether-linked dimers are active as photosensitizing agents.

EXAMPLES

The following examples are intended to illustrate but not to limit the invention.

EXAMPLE 1

Preparation of Monohydroxyethyl Monovinyl Deuteroporphyrin Ether-linked Dimer and Divinyldeuteroporphyrin Ether-linked Dimer Gaseous hydrogen bromide was bubbled into dry dichloromethane for a few minutes and then this solution (1.5 ml) was added to a solution of 2(4)-monohydroxyethyl-4(2)-monovinyldeuteroporphyrin dimethyl ester (50 mg) in dry dichloromethane and the mixture was stirred at ambient temperature for 3 min. To this solution was then added 2(4)-monoacetyl-4(2)-monohydroxyethyl deuteroporphyrin dimethyl ester (50 mg) dissolved in dichloromethane (2 ml) and the mixture was stirred at ambient temperature for 1 hr under nitrogen. Water was then added to the solution, the aqueous phase was neutralized with diluted sodium hydroxide solution and the mixture was extracted with dichloromethane.

The organic extracts were washed with water, dried (sodium sulfate) and the extract was chromatographed on alumina (Grade 1) to separate the dimer porphyrins from the monomers.

The dimer fraction, in dichloromethane (10 ml), was reduced by treatment with an ice cold solution of sodium borohydride (25 mg) in methanol (2 ml) for 30 min. The reaction was quenched by the addition of a small amount of dilute acetic acid, the organic phase was separated, washed with water and dried (sodium sulfate) to give a residue.

The residue was chromatographed on silica to yield the divinyl ether linked dimer, followed by the monovinyl monohydroxyethyl ether linked dimer and the dihydroxyethyl ether linked dimer. The major product is the monovinyl monohydroxyethyl compound.

The recovered esterified dimers can be hydrolyzed by dissolving the esters (40 mg) in tetrahydrofuran (2 ml) and sodium hydroxide solution (0.2M, 2 ml). The mixture is stirred under nitrogen for 16 hr at room temperature. The solution is then diluted with tetrahydrofuran/dichloromethane (1:1) and poured into water. The pH of the aqueous layer is adjusted to approximately 5 and the mixture is extracted with tetrahydrofuran/dichloromethane (1:1). The organic extracts are washed twice with water and the solvent is removed under reduced pressure to yield the corresponding acid.

EXAMPLE 2

Activity of the Dimers

The ability of the dimers prepared in Example 1 to effect photosensitization of tumors was assessed as follows:

Lewis lung carcinoma cells (Dr. L. Dent, Flinders Medical Centre), are transplanted into the back of C57BL mice by subcutaneous injection of approximately $10^6$ cells per mouse. After 7-10 days, when the tumors are 5-7 mm in diameter, mice in groups of 10 are given test compounds (25-60 mg/kg, i.p. or i.v.). Twenty-four hours later mice are anesthetized, the fur over the tumor shaved, and a 1 cm diameter area over the tumor is irradiated with red light as specified. Mice are palpated daily for recurrence of tumor. The end point is the number of days for 5 out of 10 mice to regrow palpable tumor.

Light can be supplied by a gold metal vapor laser (Quentron Optica Pty. Ltd.) with wavelength 627.8 nm. This laser generates average light intensities of 400 mW coupled to a 400 um quartz fiber and can be positioned to create a 1 cm diameter spot.

Alternatively, an incandescent filament lamp fitted with a perspex lens 10 mm in diameter and 50 mm length delivers 2.5 W uniformly over 1 cm at 620–720 nm wavelength. The effective light flux at 630 nm is 890 mW, determined from the relative light flux absorbed by HPD at 630 nm (Wilkach, 1982, unpublished data). When this light source is used, the skin of the mouse is sprayed with water and irradiated in 50 sec exposures with 10 sec pauses to prevent thermal effects.

When the compounds of the invention were tested in this system, they were comparably active to the Photofrin® II composition. Data were recorded as "TC$_{50}$"—the first time (in days) after treatment for the tumor to regrow to a palpable stage (as shown in Table 1).

TABLE 1

|  | TC$_{50}$ |
|---|---|
| Photofrin ® II composition | 7 days |
| DHE | 0 days |
| (1) where one R = hydroxyethyl, one R = vinyl | 3 days |
| (1) where both R = vinyl | 7 days |
| HpD | 5 days |

I claim:
1. A compound of the formula

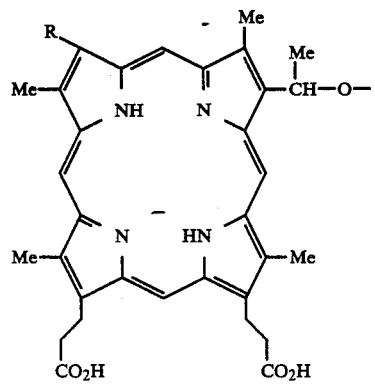

(1)

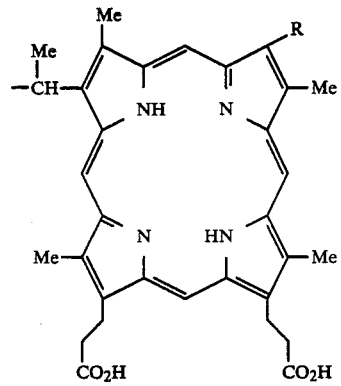

wherein one R is vinyl and the other R is 1-hydroxyethyl or vinyl and the pharmaceutically acceptable esters and salts thereof, in isolated form.

2. The compound of claim 1 wherein the ester is a methyl or ethyl ester.

3. The compound of claim 1 wherein one R is vinyl and the other R is 1-hydroxyethyl.

4. The compound of claim 1 wherein both R are vivyl.

5. A pharmaceutical composition which consists essentially of the compound of formula 1 as active ingredient along with a pharmaceutically acceptable excipient.

6. A method to detect or photosensitize a target biological substrate which comprises contacting said target with an effective amount of the compound of claim 1 or a pharmaceutical composition thereof and irradiating said target with light absorbed by said compound.

7. A conjugate which consists essentially of the compound of claim 1 covalently bound to an immunoglobulin or immunologically reactive fragment thereof or a receptor ligand.

8. A pharmaceutical composition useful for labeling malignant tissue which comprises the compound of claim 1 associated with label.

9. A pharmaceutical composition which consists essentially of the conjugate of claim 7 as active ingredient, along with a pharmaceutically acceptable excipient.

* * * * *